US00PP37293P2

(12) United States Plant Patent
Grosser

(10) Patent No.: US PP37,293 P2
(45) Date of Patent: Mar. 3, 2026

(54) HYBRID LIME PLANT NAMED 'C4-5-14'

(50) Latin Name: ***Citrus* sp.**
Varietal Denomination: C4-5-14

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/307,406

(22) Filed: Aug. 22, 2025

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./202
See application file for complete search history.

(56) References Cited

U.S. PATENT DOCUMENTS

PP27,298 P3 10/2016 Grosser

*Primary Examiner* — Susan McCormick Ewoldt
(74) *Attorney, Agent, or Firm* — Koenig IP Works, PLLC; Katherine Koenig

(57) ABSTRACT

A new and distinct cultivar of hybrid lime (*Citrus* sp.) plant named 'C4-5-14', characterized by near-seedlessness, high productivity, HLB tolerance, consistent aroma, juiciness, and multiple blooms throughout the year. The new cultivar 'C4-5-14' is suitable for the fresh fruit industry and for dooryard trees. The new cultivar 'C4-5-14' is a triploid hybrid from an interploid cross of alletetraploid somatic hybrid ['Santa Teresa' lemon+'Lakeland' limequat] x diploid 'Cook Eureka' lemon.

10 Drawing Sheets

Genus and species: *Citrus* sp.
Cultivar denomination: 'C4-5-14'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The present invention relates to a new and distinct cultivar of hybrid lime, botanically known as *Citrus* sp., and hereinafter referred to by the name 'C4-5-14'. *Citrus* sp. is a member of Rutaceae.

The new hybrid lime cultivar 'C4-5-14' is a triploid hybrid from a zygotic seed from a tetraploid female parent. More specifically, the new hybrid lime cultivar 'C4-5-14' is a complex hybrid of *Citrus limon, Citrus aurantifolia*, and *Fortunella japonica*, namely, it is the result of an interploid cross of allotetraploid somatic hybrid ['Santa Teresa' lemon+'Lakeland' limequat] (seed parent) x diploid 'Cook Eureka' lemon (pollen parent; unpatented). Neither 'Santa Teresa' nor 'Lakeland' are patented. The original tree was a zygotic seedling planted (on its own roots) in Lake Alfred, Florida, in 2014. True-to-typeness through propagation was demonstrated by planting trees produced from pathogen-free PTP (Parent Tree Program) budwood on 'UFR-5' rootstock in Lake Alfred, Florida, in November of 2021.

Plant Breeder's Rights for this cultivar have not been applied for. The new hybrid lime cultivar 'C4-5-14' has not been made publicly available more than one year prior to the filing of this application.

SUMMARY OF THE INVENTION

The new hybrid lime cultivar 'C4-5-14' has not been observed under all possible environmental conditions. The phenotype of the new cultivar may vary with variations in environment and cultural practices such as temperature, light intensity, fertilization, irrigation, and application of plant growth regulators without any change in genotype.

The new hybrid lime cultivar 'C4-5-14' was selected from a population of triploid seedlings from the cross outlined above for its initial productivity and subsequent huanglongbing (HLB, *Citrus* greening) tolerance. Fruit of the new cultivar resembles 'Key' (Mexican) lime (*Citrus* x *aurantiifolia*, also referred to as Mexican lime) more so than Persian lime (*Citrus* x *latifolia*) for size, color and flavor. Some fruit can be larger than that of 'Key' lime, but the average size is smaller than that of Persian Lime. Like 'Key' lime, fruit of the new cultivar 'C4-5-14' turns yellow on the tree when over-ripe. The interior color of the fruit becomes more yellow as the fruit matures, and does not have a green interior like Persian limes. Fruit of 'C4-5-14' is consistently aromatic and juicy, with a strong lime fragrance. Trees exhibit multiple blooms throughout the year, so there is usually mature fruit available on the tree most of the year. This makes 'C4-5-14' an excellent candidate for the dooryard *Citrus* market, as well as the fresh fruit industry. Fruit right off the tree has a 'waxed' appearance.

There are no data supporting long-term field performance or yield for the new cultivar 'C4-5-14'. However, multiple trees grown on 'UFR-5' (U.S. Plant Pat. No. 27,298) rootstock that were planted in November of 2021 grew vigorously without individual protective covers (IPCs) and without antibiotic treatments, and these trees began fruiting heavily in spring of 2024. No obvious tree-debilitating disease problems have been observed in the trees or fruit of trees of the new cultivar that have been grown so far. 'C4-5-14' needs to be tested on multiple rootstocks to identify any incompatibilities that might arise, as the 'Cook Eureka' lemon (unpatented) and kumquat parentage have both shown incompatibility issues with some trifoliate hybrid rootstocks.

Plant of the new hybrid lime cultivar 'C4-5-14' differ from plants of the female parent, allotetraploid somatic hybrid ['Santa Teresa' lemon+'Lakeland' limequat], in the following characteristics:

1. Unlike the female parent, the fruit of 'C4-5-14' is nearly seedless.
2. Fruit of 'C4-5-14' is smaller in size than that of the female parent.
3. Although the female parent fruit has a very nice aroma, the aroma of 'C4-5-14' fruit is much more limey.

Plant of the new hybrid lime cultivar 'C4-5-14' differ from plants of the male parent, diploid 'Cook Eureka' lemon, in the following characteristics:

1. Unlike the male parent, the fruit of 'C4-5-14' is nearly seedless.
2. The aroma and flavor of fruit of 'C4-5-14' are limey, not lemony like those of 'Cook Eureka'.
3. Fruit size of 'C4-5-14' is smaller than that of 'Cook Eureka'.

DESCRIPTION OF THE FIGURES

The accompanying photographs (as shown in FIGS. 1-12) illustrate the overall appearance of the new hybrid lime cultivar 'C4-5-14'. These photographs show the colors as true as can be reasonably obtained in colored reproductions of this type. Colors in the photographs may differ slightly from the color values cited in the detailed botanical description, which accurately describe the colors of the new hybrid lime cultivar.

DETAILED BOTANICAL DESCRIPTION OF THE CULTIVAR

Figure 1:
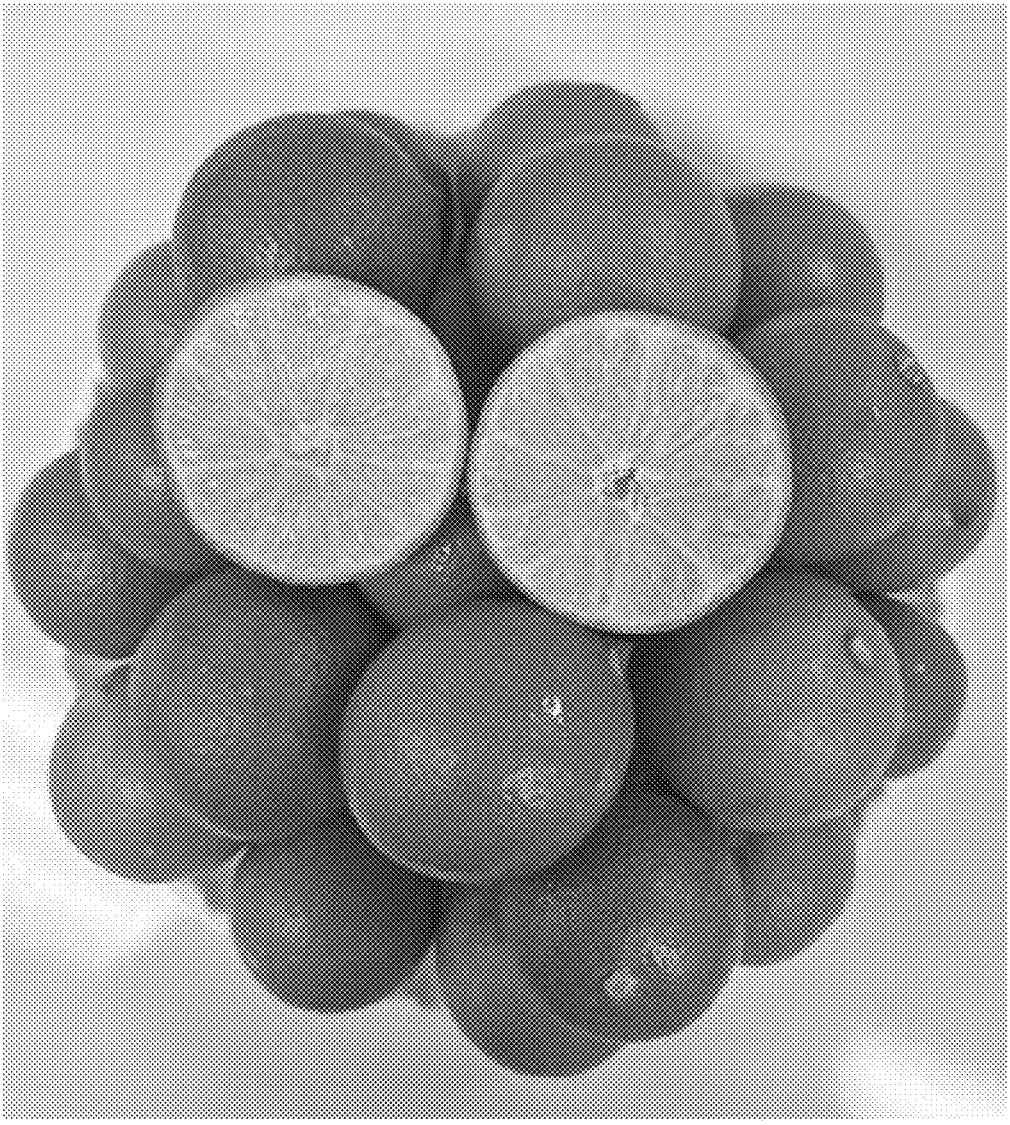
FIG. 1 shows whole and cut fruit of the new hybrid lime cultivar 'C4-5-14' in September 2024.
Figure 2:
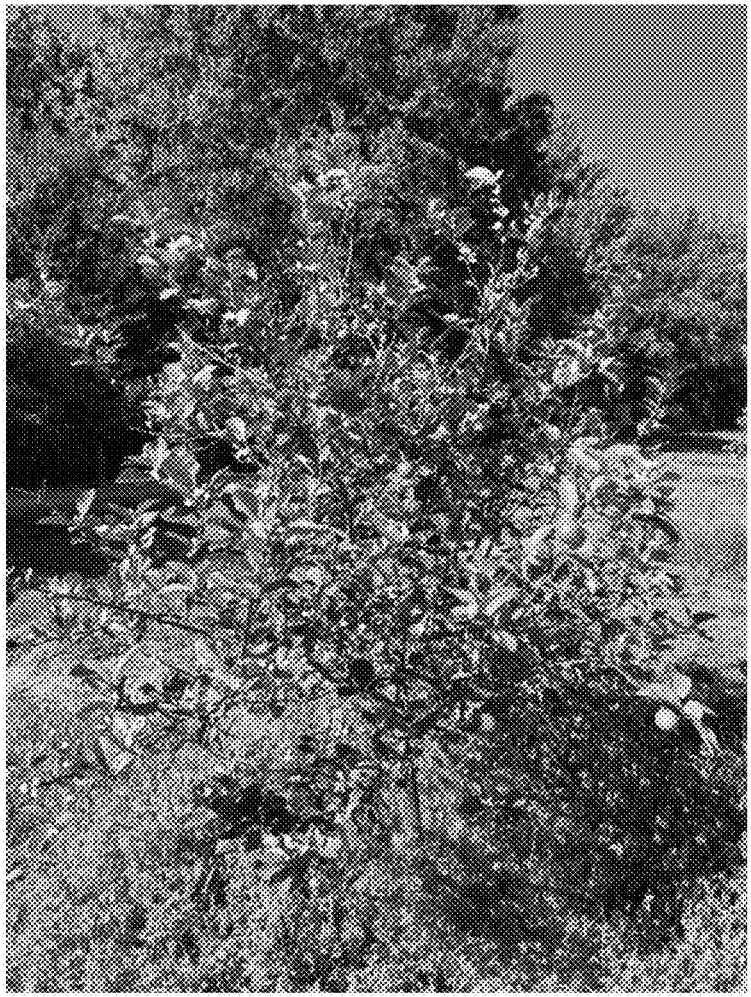
FIG. 2 shows the overall tree growth habit of the new hybrid lime cultivar.
Figure 3:
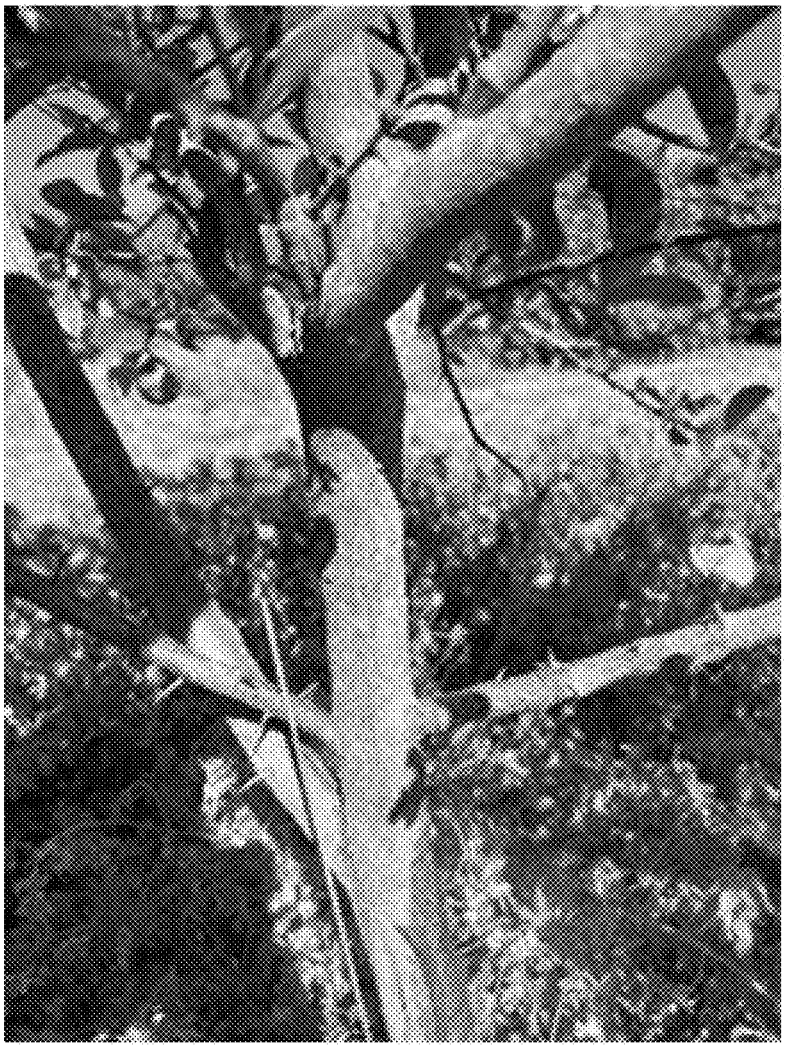
FIG. 3 shows a trunk and branches of a tree of the new hybrid lime cultivar.
Figure 4:
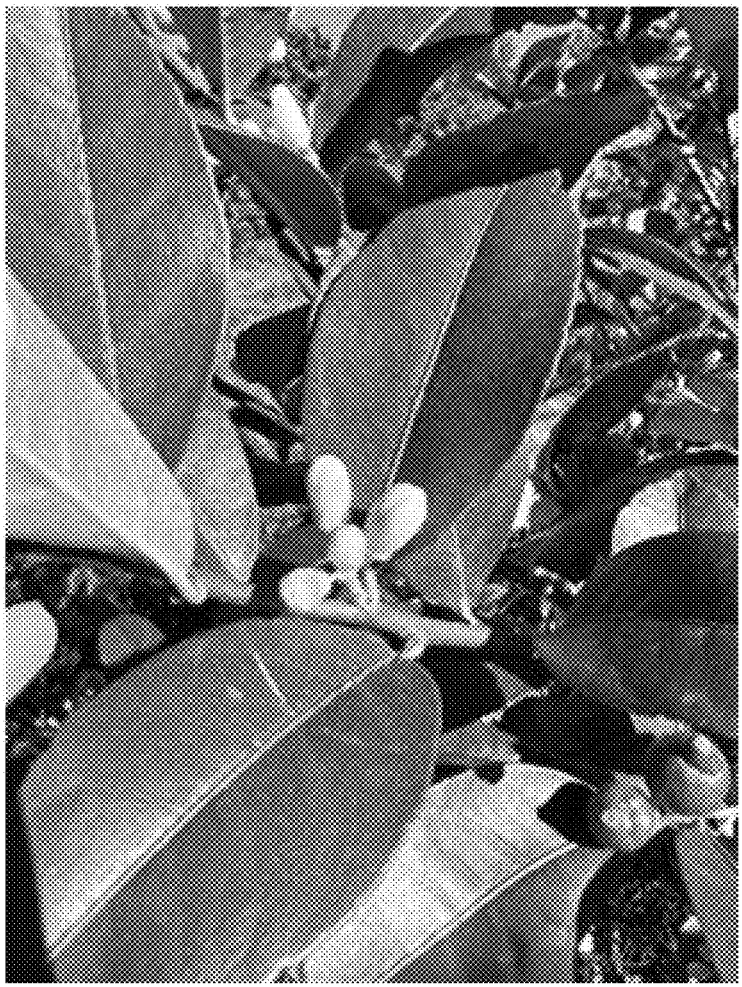
FIG. 4 shows a leaves and a flower cluster of the new hybrid lime cultivar, the flower cluster including buds in different development stages.
Figure 5:
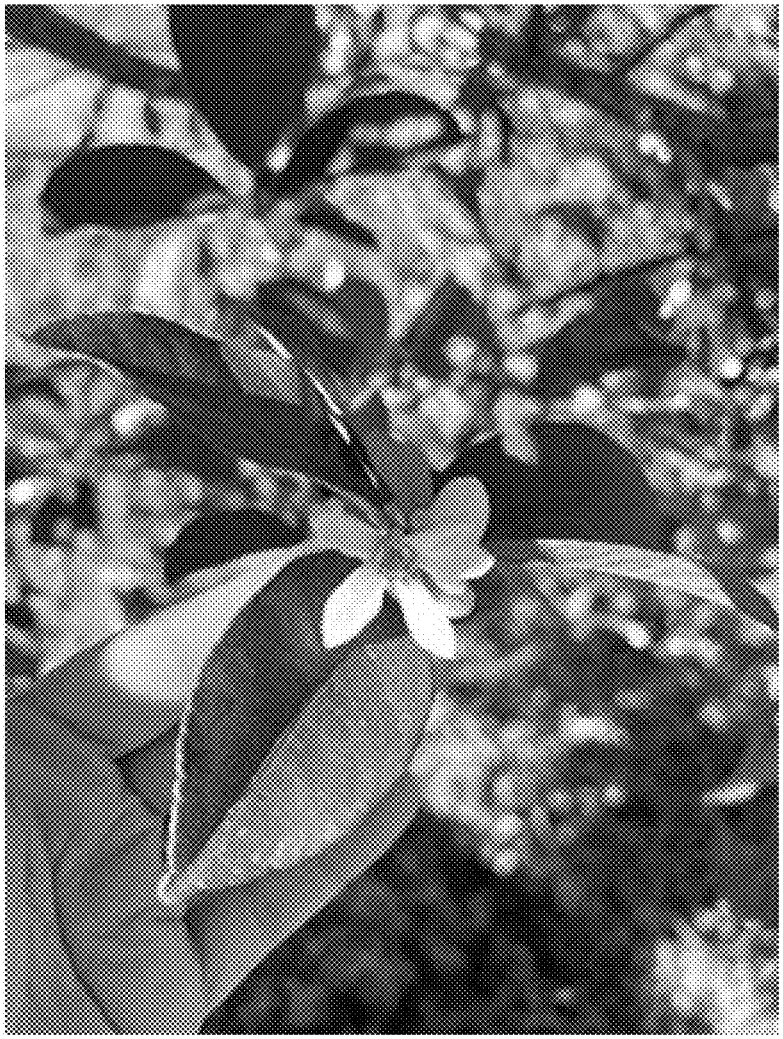
FIG. 5 shows a leaves and a flower cluster of the new hybrid lime cultivar, the flower cluster including a mature opened flower and an unopened flower.
Figure 6:
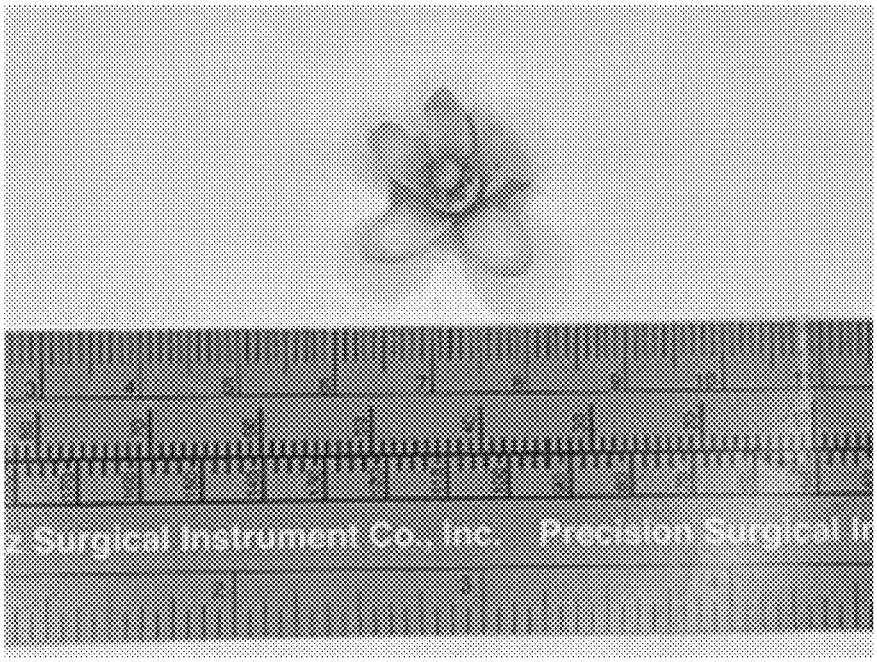
FIG. 6 shows a top view of a fully expanded flower of the new hybrid lime cultivar, with a ruler shown for size comparison.
Figure 7:
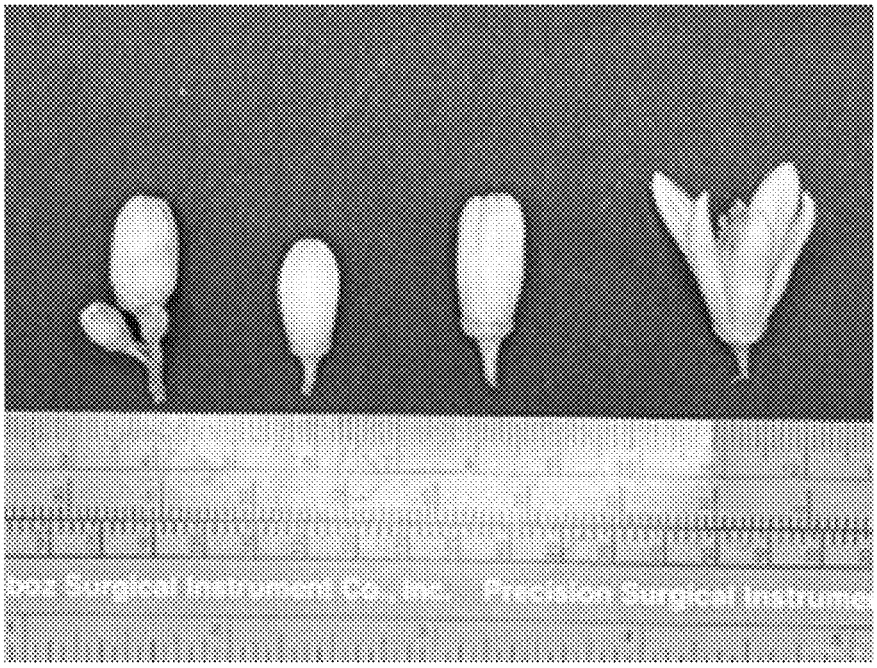
FIG. 7 shows a side view of flowers of the new hybrid lime cultivar in different developmental stages, with a ruler shown for size comparison.
Figure 8:
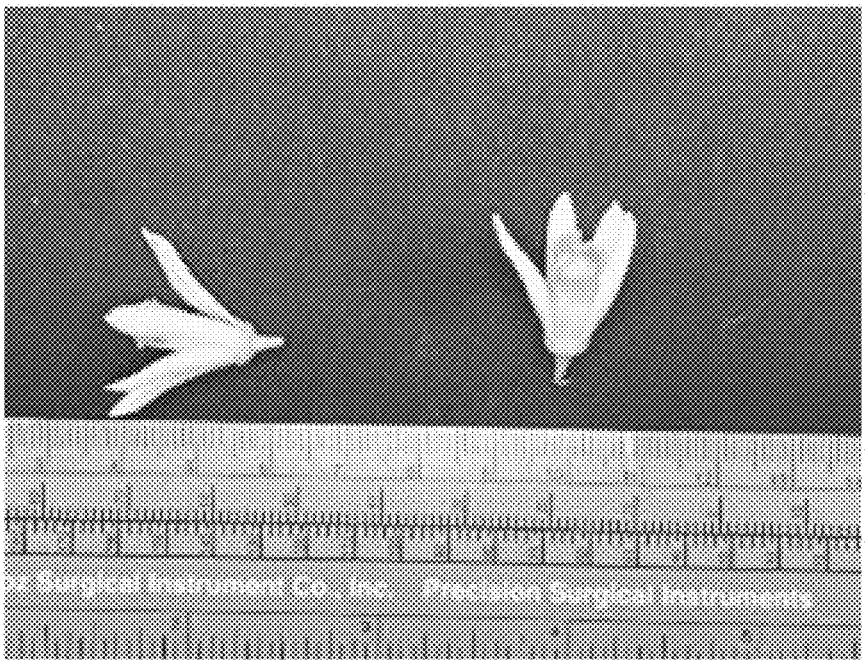
FIG. 8 shows a side view of fully expanded flower of the new hybrid lime cultivar, with a ruler shown for size comparison.
Figure 9:
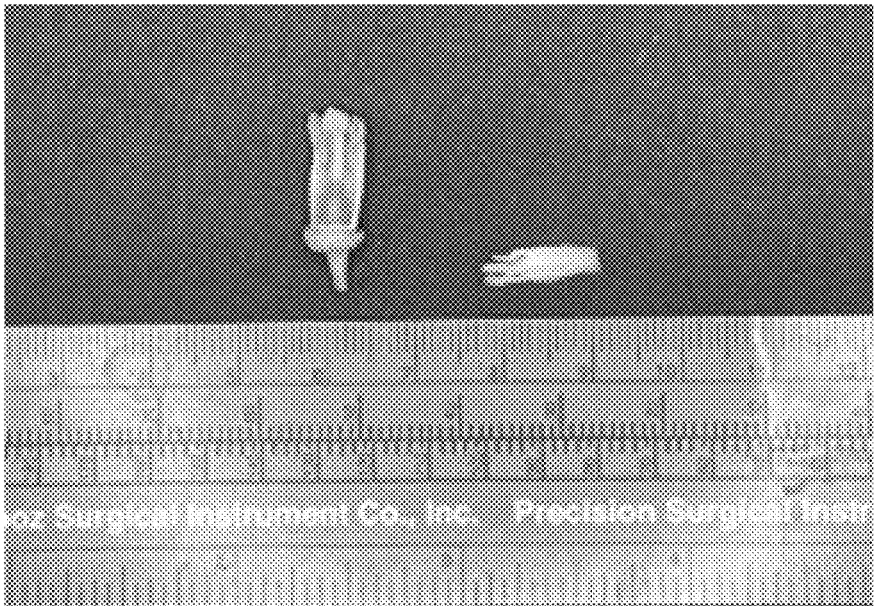
FIG. 9 shows a side view of flowers of the new hybrid lime cultivar, with petals removed to show reproductive organs and a ruler shown for size comparison.
Figure 10:
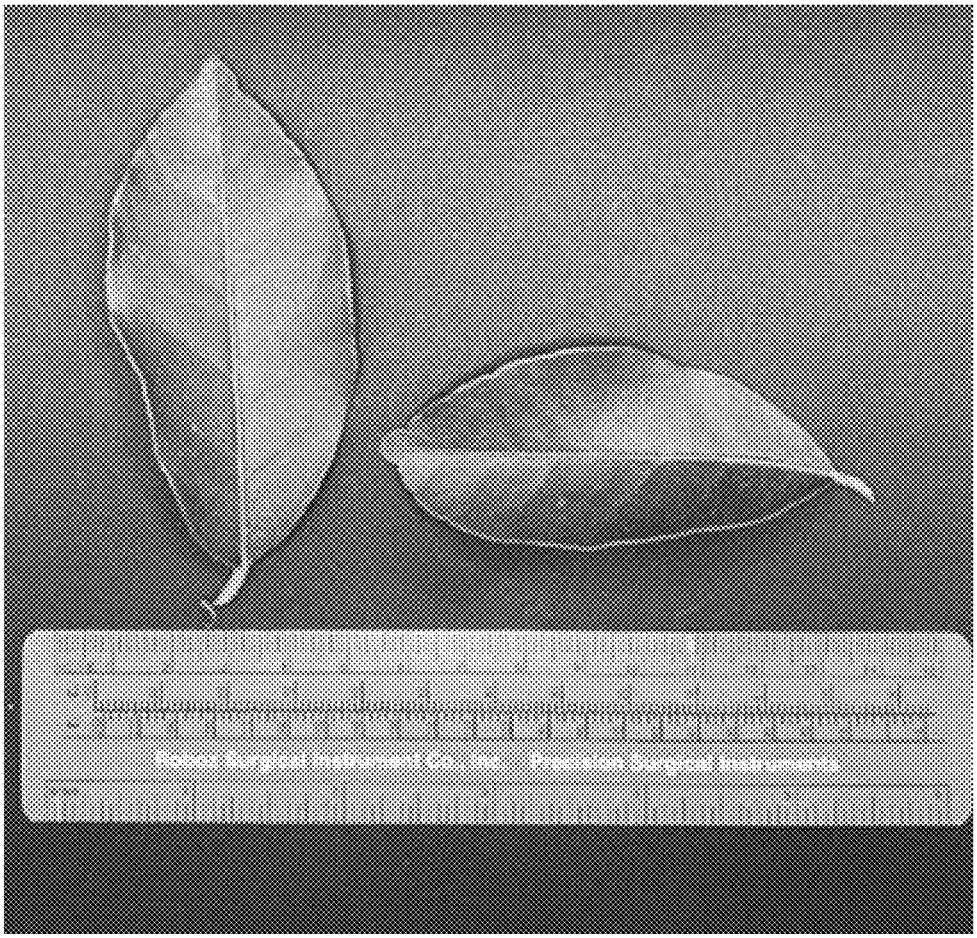
FIG. 10 shows fully expanded leaves of the new hybrid lime cultivar, with a ruler shown for size comparison.
Figure 11:
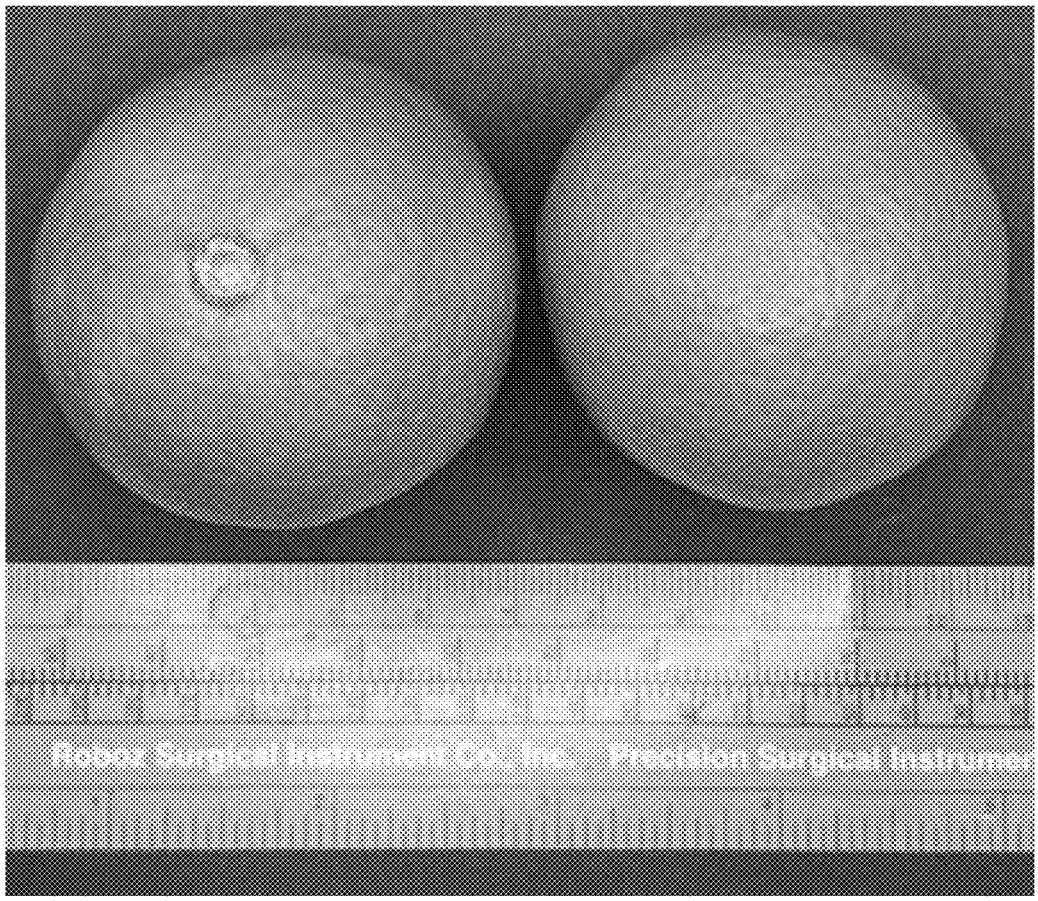
FIG. 11 shows fruit of the new hybrid lime cultivar from both the pedicel end and the apex end, with a ruler shown for size comparison.
Figure 12:
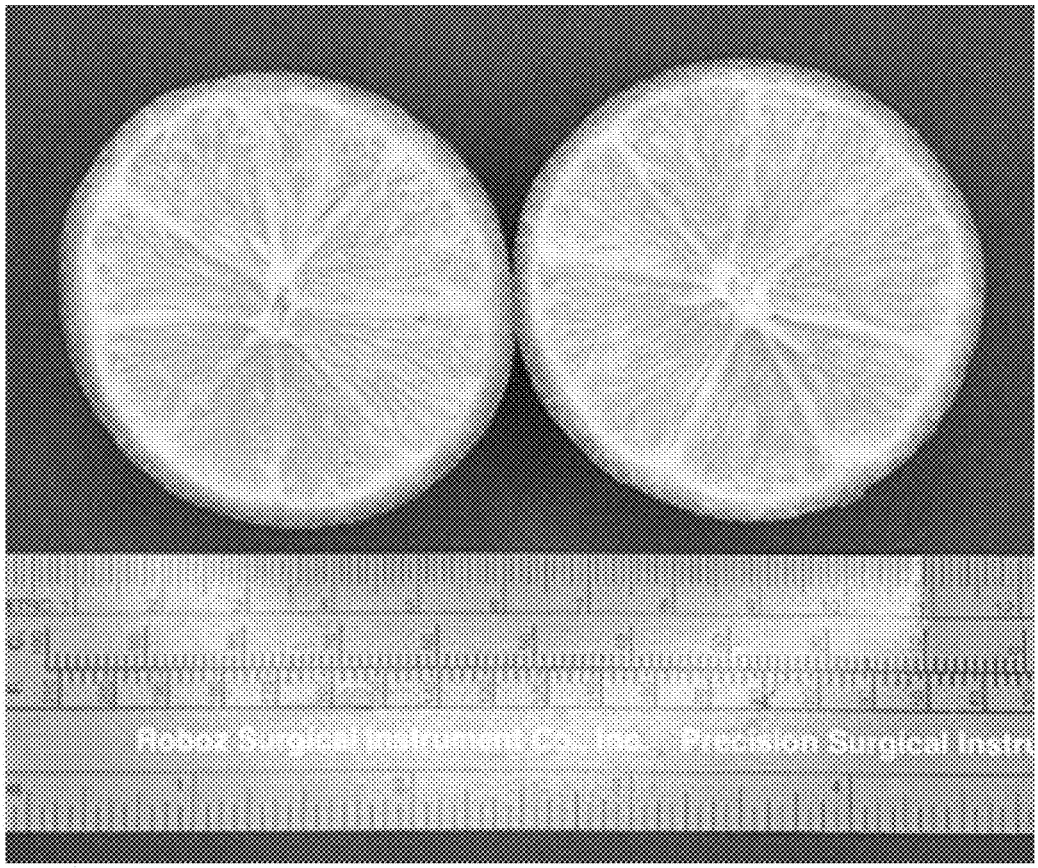
FIG. 12 shows fruit the new hybrid lime cultivar that is cut transversely, with a ruler shown for size comparison.

In the following description, color references are made to The Royal Horticultural Society (R.H.S.) Colour Chart, 1986 Edition, except where general terms of ordinary dictionary significance are used.

BOTANICAL DESCRIPTION

Botanical classification: Complex hybrid of *C. limon, C. aurantifolia*, and *Fortunella japonica.*

*Family*.—Rutaceae.

*Botanical name*.—Hybrid lime (*Citrus* sp.).

*Common name*.—Hybrid lime.

*Cultivar*.—'C4-5-14'.

Parentage: Triploid hybrid from an interploidy cross of alletetraploid somatic hybrid ['Santa Teresa' lemon+ 'Lakeland' limequat] x diploid 'Cook Eureka' lemon (pollen parent).

Tree:

*Ploidy*.—Triploid.

*Size*.—Medium.

*Width across row*.—2.43 meters on average.

*Width down row*.—2.13 meters on average.

*Tree height*.—2.2 meters on average.

*Tree canopy diameter*.—7.62 meters in diameter on average.

*Vigor*.—High.

*Density*.—Medium.

*Tree shape* (*form*).—Spreading.

*Growth habit* (*current season*).—Rounded.

*Trunk*.—Trunk diameter: Approximately 18 cm at 30 cm above the ground. Trunk texture: Rough. Trunk bark color: RHS 199C (Grey-Brown Group).

*Branches*.—Branch length: 1.36 meters on average. Branch diameter: 10 cm on average. Crotch angle: Less than 90 degrees (on average) when located in the middle of the tree, but with some being more than 90 degrees (approximately 110-115) when located on the outside of the tree. Branch texture: Less rough than the trunk. Branch color: RHS 197B (Greyed-Green-Group).

*Thorns*.—Length: 0.1-2 cm on average when present.

Leaves:

*Size* (*lamina average*).—Length: 82.1 mm on average. Width: 39.6 mm on average. L/W ratio: 2.07 on average. Thickness: Relatively thick. Type: Simple (unifoliate). Shape: Elliptical. Apex: Acute with the apex being retuse. Base: Acute. Margin: Serrulate. Leaf edges with smaller, more evenly spaced serrations than a serrated leaf.

*Surface*.—Upper surface: Smooth. Lower surface: Smooth.

*Color*.—Upper surface (adaxial): RHS 137A (Green Group). Lower surface (abaxial): RHS 146C (Yellow-Green Group).

*Petiole*.—Shape and attachment: Absence of petiole wing. Length: 8.4 mm on average. Width: 1.7 mm on average. Color: RHS 144A (Yellow-Green Group).

Flowers:

*Type*.—Hermaphrodite.

*Flower diameter*.—34.9 mm on average.

*Flower depth*.—16.1 mm on average.

*Flower blooming period*.—Blooms observed throughout the year.

*First bloom*.—March-April.

*Full bloom*.—March.

*Fragrance*.—Fragrant.

*Flower bud size*.—Length: 1 mm on average for the initial visible flower bud; 14 mm on average for the mature flower buds before opened. Diameter: 1 mm on average in the initial visible flower bud; 7 mm on average in the matured bud.

*Flower bud shape*.—Initial visible flower bud with round ball shape; mature flower bud with elongated olive shape.

*Flower bud color* (*R.H.S.*).—RHS 144C (Yellow-Green) for the initial visible flower bud; combination of RHS 60B (Red-purple Group) and RHS 155D (White Group) for mature buds.

Reproductive organs:

*Fertility*.—Appears to be self-fertile.

*Petals*.—Number: 5. Petal length: 14.9 mm on average. Petal width: 5 mm on average. Petal shape: Recurved/cruciform. Apex shape: Smooth with obtuse angle. Base shape: Obtuse. Petal color: Upper Surface: RHS 158B (Yellow-White Group). Lower surface: RHS 155D (White Group). Margin: Smooth.

*Sepal*.—Number (per flower): 5 on average. Shape: Short flat delta with acute angle at apex. Length: 2 mm on average. Width: 2.5 mm on average. Apex shape: Acute. Margin: Smooth. Sepal color: Upper surface: RHS 145D (Yellow-Green Group). Lower surface: RHS 145D (Yellow-Green Group).

*Pedicel*.—Length: 5.9 mm on average. Diameter: 1.6 mm. Color: RHS 145A (Yellow-Green Group).

*Stamen*.—Number: 22-24 per flower on average. Length: 14.4 mm on average.

*Anther*.—Length: 2.2 mm on average. Width: 1.1 mm on average. Pollen color (general): RHS 22A (Yellow-Orange Group).

*Pistil*.—Number: 1. Length: 11.9 mm on average. Color: RHS 145C (Yellow-Green Group). Style length: 6.5 mm. Style diameter: 1 mm on average. Style color: RHS 145C (Yellow-Green Group). Ovary shape: Ovate to elongate. Ovary diameter: 2.1 mm on average. Ovary color: RHS N144C (Yellow-Green Group).

Fruit:

*Size*.—Normal to medium size.

*Average weight* (*per individual fruit*).—91 grams on average.

*Length* (*height*).—58 mm on average.

*Diameter*.—54 mm on average.

*Shape* (*cross-section*).—Spherical.

*Apex*.—Round.

*Base*.—Round with a slight neck.

*Harvest*.—Date of first pick: Multiple blooms, March to April. Date of last pick: September to October.

*Fruit stem*.—Length: 8 mm on average. Diameter: 1.5 mm on average. Color RHS: RHS 144B (Yellow-Green Group).

*Rind*.—Adherence: Difficult to peel. Adherence of albedo (mesocarp) to the endocarp is strong and relatively difficult to separate. Thickness: 1.2 mm on average (thin). Texture: Firm with an excellent strong smell. Surface texture: Firm. Flavedo (epicarp): RHS 144A (Yellow-Green Group). Albedo (mesocarp): RHS 157B (Green-white Group). Endocarp: RHS 160B (Greyed-Yellow Group). Rind oil cell density: 48-56 cells/square cm. Oil Gland Size: 0.95 mm on average.

*Flesh*.—Number of segments: 8 on average. Segment length: 2 cm on average. Segment width: 1.8 cm on average. Juice: Abundant. Color: RHS 160A (Greyed-Yellow Group). Texture: Soft. Vesicles thickness: Thin Length: 12 mm on average. Diameter: 2 mm on average. Juice quality: Brix: 6.4. Acidity (average): 3.14. Ratio: 2.04. Juice color: RHS 160A (Greyed-Yellow Group). Lb solid/box: N/A.

*Seeds*.—Number: Nearly seedless (fewer than 1 seed per fruit on average). Fruit Parthenocarpy: Yes.

Resistance to disease: HLB tolerance appears to be better than that of the Mexican or 'Key' lime, but may be similar to that of the Persian lime. No symptomatic fruits of the new cultivar 'C4-5-14' have been observed on trees with HLB. *Citrus* canker has not been observed on the trees of the new cultivar grown in the field.

What is claimed is:

1. A new and distinct hybrid lime plant named 'C4-5-14' as illustrated and described herein.

* * * * *